United States Patent
Abele et al.

(10) Patent No.: US 8,414,601 B2
(45) Date of Patent: Apr. 9, 2013

(54) FLAT IMPLANT, PARTICULARLY A HERNIA MESH

(75) Inventors: Wolfgang Abele, Tuttlingen/Donau (DE); Franz-Josef Kupferschmid, Emmingen-Liptengen (DE); Erich Odermatt, Schaffhausen (CH); Erhard Müller, Stuttgart (DE); Hans-Gerd Schmees, Wannweil (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 12/281,009

(22) PCT Filed: Mar. 3, 2007

(86) PCT No.: PCT/EP2007/001838
§ 371 (c)(1),
(2), (4) Date: Oct. 22, 2008

(87) PCT Pub. No.: WO2007/101630
PCT Pub. Date: Sep. 13, 2007

(65) Prior Publication Data
US 2009/0149875 A1    Jun. 11, 2009

(30) Foreign Application Priority Data
Mar. 9, 2006   (DE) .......................... 10 2006 011 903

(51) Int. Cl.
*A61B 17/08* (2006.01)
*B32B 19/00* (2006.01)

(52) U.S. Cl.
USPC .......................................... 606/151; 428/357

(58) Field of Classification Search ............... 428/357, 428/131, 141, 190, 426; 623/1.32, 1.5; 606/151
See application file for complete search history.

(56) References Cited

U.S. PATENT DOCUMENTS

| | | | |
|---|---|---|---|
| 6,737,371 B1 * | 5/2004 | Planck et al. | 442/304 |
| 6,966,918 B1 | 11/2005 | Schuldt-Hempe et al. | |
| 2001/0019930 A1 * | 9/2001 | Masetti | 442/344 |
| 2007/0237809 A1 * | 10/2007 | Phaneuf et al. | 424/445 |

FOREIGN PATENT DOCUMENTS

| | | |
|---|---|---|
| DE | 3830005 | 11/1989 |
| DE | 19954166 | 5/2001 |
| DE | 199 42 611 C1 | 7/2001 |
| DE | 19942611 | 7/2001 |
| DE | 10307946 | 9/2004 |
| DE | 10353930 | 2/2005 |
| EP | 0 797 962 B1 | 10/1997 |
| EP | 1 099 422 B1 | 5/2001 |
| EP | 1099422 | 8/2005 |
| EP | 1 600 118 A1 | 11/2005 |
| WO | 01/15625 A1 | 3/2001 |
| WO | 02/35984 A2 | 5/2002 |

* cited by examiner

*Primary Examiner* — Corrine M McDermott
*Assistant Examiner* — Christina Lauer
(74) *Attorney, Agent, or Firm* — DLA Piper LLP (US)

(57) ABSTRACT

A flat implant, particularly a hernia mesh, has the form of a textile net having an opening and made from non-resorbable monofilament yarns. The net includes yarns of different thicknesses which run parallel to each other.

17 Claims, 3 Drawing Sheets

FLAT IMPLANT, PARTICULARLY A HERNIA MESH

RELATED APPLICATIONS

This is a §371 of International Application No. PCT/EP2007/001838, with an international filing date of Mar. 3, 2007 (WO 2007/101630 A1, published Sep. 13, 2007), which is based on German Patent Application No. 102006011903.7, filed Mar. 9, 2006.

TECHNICAL FIELD

This disclosure relates to a flat implant, particularly a hernia mesh, in the form of a textile net having openings and made from non-resorbable monofilament yarns.

BACKGROUND

Various types of hernia mesh are known. They are usually flat, wide-meshed, warp-knitted textiles made from polypropylene monofilament yarns.

Hernia meshes are normally introduced through smaller openings in the abdomen and should unfurl as easily as possible inside the abdomen. They should lie against the internal wall of the abdomen or become embedded in the intermediate layers. On the one hand, it is desirable to implant the smallest possible amount of foreign body, since it has been shown that this avoids undesirable rejection and cicatrization that are common with relatively stiff hernia meshes having a large weight per unit area. On the other hand, when hernia meshes have a low weight per unit area, i.e., such as those made from thin monofilament yarns, problems with material unfurling may occur, since these types of hernia meshes have a low elastic recovery and cannot unfurl easily after they have been inserted into the abdominal cavity.

To solve these problems, combined hernia meshes have been developed, which consist of a basic structure, which is usually made from a non-resorbable material, with a reinforcing structure superimposed on it, which is usually made from a resorbable material. These independent, warp-knitted structures are usually produced on single- or two-bar machines and are disclosed in EP 0 797 962 B1, EP 1 099 422 B1 and DE 199 42 611 C1, for example. The advantage of hernia meshes made from a combination of resorbable and non-resorbable yarns is that they have the required stiffness for implantation. Once they have been implanted, the resorbable yarns degrade, leaving behind the relatively lightweight, warp-knitted textile made from non-resorbable yarns. Since the composite warp-knitted textiles are made up of two independent warp-knitted textiles, which are joined together during the knitting process, an intact warp-knitted textile made from non-resorbable yarns remains after the resorbable yarns have been resorbed. However, the disadvantage of these types of composite warp-knitted textiles is that they are complicated to produce.

SUMMARY

We provide a flat implant including a hernia mesh, in the form of a textile net having openings and made from non-resorbable monofilament yarns, wherein the net has yarns of different thicknesses which run substantially parallel to each other.

BRIEF DESCRIPTION OF THE DRAWINGS

Further characteristics are illustrated in the following description, in conjunction with the drawings. In this case, the various characteristics can either be realized individually in their own right, or else they may be realized in combination with each other.

DETAILED DESCRIPTION

Figure 1:
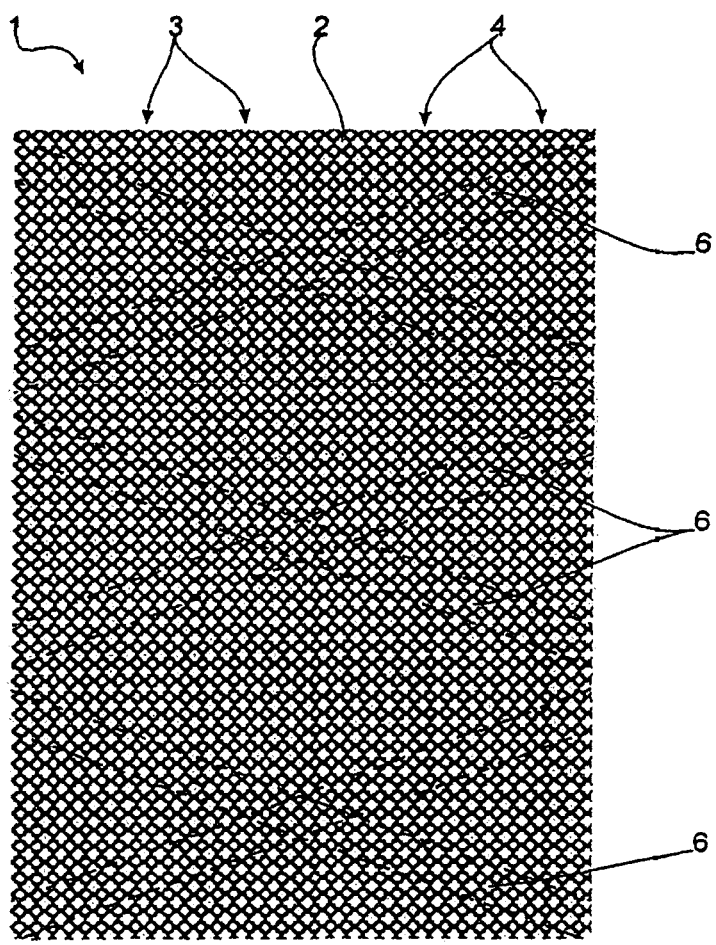
FIG. 1 is a top plan view of one of our meshes.

Our mesh comprises yarns of different thicknesses running parallel to each other. We thus provide for the processing of thicker and thinner monofilament yarns in the mesh, each made from a non-resorbable material. The thicker yarns are responsible for providing the necessary stiffness, which ensures that the mesh can unfurl easily, and the inner yarns desirably reduce the amount of foreign body that has to be implanted. Parallel running refers to the coarse construction of the textile material. There may be deviations from parallel running within the fine construction, depending on the particular textile construction.

Surprisingly, we found that it is not necessary to use the thicker, and consequently stiffer yarns, over the entire area of the mesh. In fact, it is sufficient for the mesh to incorporate so-called "stiffening ribs," which aid the unfurling process.

The meshes are usually meshes that have been heat-set. Among other things, this prevents undesirable fraying. The tensioned mesh is heat-set by heating to temperatures below the softening range of the polymer material. Stiffening elements, which may be provided in addition to or instead of the thicker yarns, may also be formed by increasing the heat-setting effect along stripes, so that the monofilament yarns are sintered mainly with each other at the intersecting points. These heat-set stripes may run in any direction, e.g., longitudinally, transversely and/or diagonally. They may also cross over each other. An annular arrangement is also possible. The heat-set stripes can be produced by applying heated heat-sealing bars.

A particular advantage is if the yarns having different thicknesses basically only run in a longitudinal direction of the textile net. This produces anisotropic reinforcement, which is quite adequate for use in practice.

We provide warp-knitted nets, especially nets having a single-jersey warp-knitted construction. This means that the yarns having different thicknesses lie within one construction in a warp-knitted structure, i.e., that the net can be formed easily in the same way as a known single-jersey warp-knitted net, whereby yarns of different thicknesses instead of yarns of the same thickness are provided. The yarns having different thicknesses, therefore, preferably lie in the same textile construction and alternate with each other in the net construction. Normally, it is adequate for just two different yarn thicknesses to be used in the textile net, and this arrangement is preferable.

It is preferable for at least two yarns of one thickness to run next to each other. This means that yarns having the same thickness form longitudinal stripes in the warp-knitted textile, which preferably have a different width. The number of thinner yarns is preferably higher than the number of thicker yarns.

This can achieve the desired reduction in weight. The ratio of thinner yarns to thicker yarns is preferably in the range of about 10:1 to about 2:1. Consequently, 10 thinner yarns may run between two reinforcing yarns, i.e., thicker yarns. However, it is also possible, for example, for 2 or more reinforcing yarns to run parallel to each other, with 5 to 20 thinner yarns positioned in-between them, for example.

The stiffness of the hernia mesh or its tendency to unfurl over the area can be varied, thanks to an irregular arrangement of the various yarns, for example, by having different distances between the yarns or a different number of yarns running-parallel to each other. This is particularly advantageous if hernia meshes of a predetermined size and predetermined characteristics are being produced. Under normal circumstances, i.e., in those instances where the surgeon cuts a hernia mesh of the requited size from a large, prefabricated mesh, meshes having the same characteristics over their entire area are desirable. In these cases in particular, it is therefore preferable for the thicker yarns and the thinner yarns to alternate with each other in a repeating pattern. It is also preferable for the yarns having different thicknesses to be made from the same material, even though this is not obligatory. Particularly suitable materials for the yarns are polypropylene, polyurethane, polyethylene terephthalate, polyvinylidene difluoride and the like.

Preferably, the thicker yarns are about 15 to about 60%, especially about 20 to about 40% thicker than the thinner yarns. Consequently, thicker yarns having a yarn diameter of about 120 to about 200 μm, especially about 135 to about 165 μm, have proven to be particularly suitable. Suitable thinner yarns preferably have a thickness of about 80 to about 150 μm, especially about 110 to about 140 μm.

The openings in the mesh may have various sizes and shapes. The loose opening in the openings in the mesh usually measures between about 0.5 and about 5 mm. Depending on the type of construction, especially the warp-knitted construction, the openings may be quadrangular, especially rhombic-shaped, pentagonal-shaped, especially diamond-shaped, or hexagonal-shaped, especially honeycomb-shaped. Meshes having different, alternating opening shapes are also possible.

Figure 3:
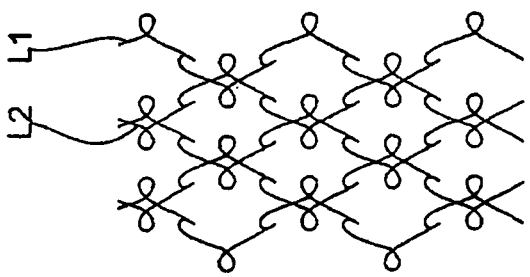
FIG. 3 is an exploded view of the construction of the mesh shown in FIG. 1.
Figure 4:
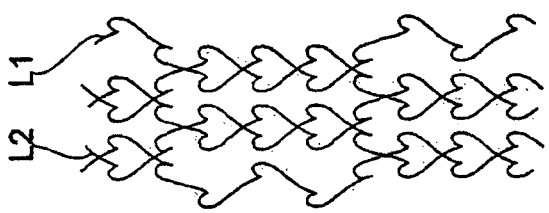
FIG. 4 is an exploded view of the construction of a mesh having a honeycomb structure.
Figure 5:
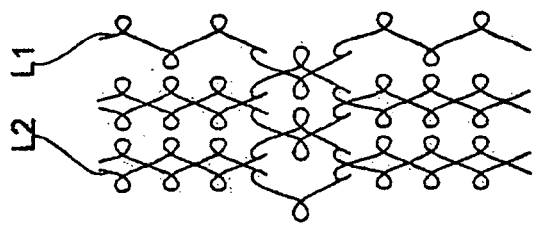
FIG. 5 is an exploded view of the construction of the mesh shown in FIG. 2.

For example, a mesh may be in the form of a warp-knitted textile having a filet construction and the lapping arrangement as shown in FIG. 3, whereby the openings are rhombic-shaped. The mesh may be in the form of a warp-knitted textile having a filet construction and the lapping arrangement as shown in FIG. 4, whereby the openings are honeycomb-shaped. Furthermore, the mesh may have a filet construction and the lapping arrangement as shown in FIG. 5, whereby honeycomb-shaped rows of openings and rhombic-shaped rows of openings alternate with each other in the longitudinal direction, and the honeycombs and rhombic shapes are staggered in relation to each other in the longitudinal direction. L1 and L2 in FIGS. 3 to 5 relate to guide bar 1 and guide bar 2 in each case.

The width of the reinforcing stripes may vary from between about 2 and about 8 mm, depending on the number of adjacent reinforcing yarns, whereby a lower range of about 2 to about 4 mm is preferred, since it has been shown that reinforcing yarns as individual yarns already produce an adequate level of stiffness in the warp-knitted composite. The width of the stripes made from the thinner yarns is preferably about 5 to about 25 mm, whereby an upper range of about 20 to about 25 mm is preferred in this case.

The weight per unit area of the mesh may be between about 25 and about 85 g/m². It is advantageous for the weight per unit area of the mesh to be between about 30 and about 80 g/m², whereby a weight per unit area of about 35 to about 70 g/m² is preferred. Especially preferred are weights per unit area of about 40 to about 65 g/m².

The meshes may be pretreated to promote their in-growth, on the one hand, and to prevent undesirable adhesion, on the other hand. Consequently, the yarns, especially if they are made from a hydrophobic material, may have a surface coating or they may undergo a hydrophilic pretreatment, for example, by plasma treatment. To avoid adhesion, the entire surface of one side of the mesh may be finished, especially coated, with a membrane-like film made from an anti-adhesive material. The meshes may also have so-called "guide lines," especially in the form of colored longitudinal stripes. In this case, it is advisable for the reinforcing yarns to have a different color to the basic material. But thinner yarns can also be dyed.

The surface of the monofilaments in the implant may be treated with wound-healing and/or antibiotic substances.

The mesh shown in FIG. 1 is a heat-set hernia mesh (1) in the form of a single-jersey warp-knitted textile in a filet construction, with the lapping arrangement as shown in FIG. 3. The warp-knitted textile has a net-like structure, in which rhombic-shaped openings (2) are arranged in longitudinal rows, whereby each adjacent row is staggered on a gap. The rhombic-shaped openings have a loose mesh width of approximately 3 mm. The warp-knitted textile has a striped construction, in which wide longitudinal stripes (3) alternate regularly with narrow longitudinal stripes (4). The wide longitudinal stripes are made up of monofilament polypropylene yarns, which have a yarn thickness of approximately 120 μm. On the other hand, the narrow longitudinal stripes are made from monofilament polypropylene yarns having a larger thickness of approximately 150 μm. The narrow longitudinal stripes have a width of approximately 3 mm and the wide longitudinal stripes have a width of approximately 15 mm, which corresponds to ratio of thicker yarns to thinner yarns of 1:5. The hernia mesh with the rhombic-shaped openings has largely isometric stretch and breaking elongation in the longitudinal and transverse directions.

The thicker yarns, i.e., those forming the narrow stripes, are deep-dyed, whereas the yarns in the narrow stripes are colorless. This produces parallel guide lines, which make it easier to place the hernia mesh in the required position during implantation. FIG. 1 shows additional thermal reinforcing elements 6, which run diagonally and are shown by dashed lines.

Figure 2:
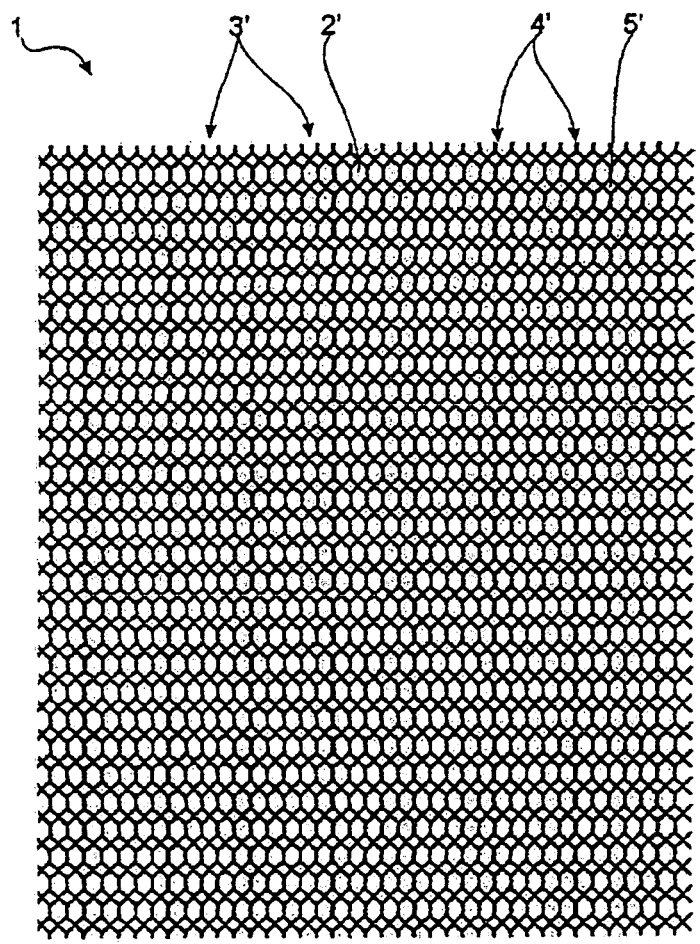
FIG. 2 is a top plan view of another one of our meshes.

The mesh in FIG. 2 is a heat-set hernia mesh (1') in the form of a simple warp-knitted textile in a filet construction. The warp-knitted textile has a net-like construction, in which hexagonal openings (2') and rhombic-shaped openings (5') alternate with each other. The hexagonal openings (2') are arranged adjacent to each other in longitudinal and transverse rows. The rhombic-shaped openings (5') are also arranged in longitudinal and transverse rows, whereby they are staggered opposite to the rows of hexagonal openings and fill-in the remaining gaps. The hexagonal openings (2') have a loose mesh width of approximately 4×6 mm. The rhombic-shaped openings have a loose opening of approximately 2 mm.

The warp-knitted textile is again in the form of stripes, whereby wide longitudinal stripes (3') alternate regularly with narrow longitudinal stripes (4'). The wide longitudinal stripes consist of polypropylene monofilament yarns, which have a yarn thickness of approximately 120 μm. On the other hand, the narrow longitudinal stripes are made from monofilament polypropylene yarns having a larger yarn thickness of approximately 150 μm. The narrow longitudinal stripes (4') have a width of approximately 2.5 mm, and the wide longitudinal stripes have a width of approximately 15 mm. The narrow longitudinal stripes each border a longitudinal row of rhombic-shaped openings, which are joined to each other by simple, longitudinal connecting pieces. The ratio of rhombic-shaped openings in the transverse direction, which are formed from stronger yarns, to those that are formed from weaker yarns, is in the order of 1:4. The stronger yarns are again dark and form narrow guide lines running in the longitudinal direction.

The colored guide lines may also be present, regardless of whether the yarns are thicker or thinner. Consequently the thinner yarns, which lie next to the narrow stripes, may also be dyed darker than the other thinner yarns, so that wider, colored stripes are formed, without the actual reinforcing stripes thus having to be made wider.

The invention claimed is:

1. A flat implant comprising a hernia mesh, in the form of a textile net having openings and made from non-resorbable monofilament yarns of different thicknesses, wherein the yarns of different thicknesses run substantially parallel to each other, the implant has a number of thinner yarns that is higher than a number of thicker yarns, the thicker and thinner monofilament yarns are each made from a non-resorbable material, and the yarns of different thicknesses only run in a substantially longitudinal direction of the textile net.

2. The implant as claimed in claim 1, wherein the mesh is a warp-knitted textile.

3. The implant as claimed in claim 2, wherein the yarns having different thicknesses lie in a common warp-knitted structure and construction.

4. The implant as claimed in claim 1, wherein the yarns of different thicknesses are present in the hernia mesh and alternate with each other in the construction of the mesh.

5. The implant as claimed in claim 1, having yarns of two different thicknesses.

6. The implant as claimed in claim 1, wherein at least two yarns of the same thickness each run adjacent to each other.

7. The implant as claimed in claim 1, wherein a ratio of thinner yarns to thicker yarns is 10:1 to 2:1.

8. The implant as claimed in claim 1, wherein the thicker yarns and the thinner yarns alternate with each other in a repeating pattern.

9. The implant as claimed in claim 1, having yarns of two different thicknesses wherein the yarns having different thicknesses are made from the same material.

10. The implant as claimed in claim 1, having yarns of two different thicknesses wherein the thicker yarns are about 15 to about 60% thicker than the thinner yarns.

11. The implant as claimed in claim 1, having yarns of two different thicknesses wherein the thicker yarns have a yarn diameter of about 120 to about 200 μm and the thinner yarns have a diameter of about 80 to about 150 μm.

12. The implant as claimed in claim 1, wherein the mesh is a warp-knitted textile having a filet construction and the openings are rhombic-shaped.

13. The implant as claimed in claim 1, wherein the mesh is a warp-knitted textile having a filet construction and the openings are honeycomb-shaped.

14. The implant as claimed in claim 1, wherein the mesh is a warp-knitted textile having a filet construction and honeycomb-shaped rows of openings alternate with rhombic-shaped rows of openings in the longitudinal direction and are staggered in relation to each other in the longitudinal direction.

15. The implant as claimed in the preamble of claim 1, having reinforcing stripes formed by thermal consolidation of the mesh.

16. The implant as claimed in claim 15, wherein the thermal consolidation comprises thermal bonding of intersecting monofilament yarns.

17. The implant as claimed in claim 1, wherein the mesh is a warp-knitted textile having a single jersey construction.

* * * * *